US00PP09079P

United States Patent [19]

Hope

[11] Patent Number: Plant 9,079

[45] Date of Patent: Mar. 14, 1995

[54] ANTHURIUM PLANT NAMED PURA VIDA LAVENDER

[75] Inventor: Claude Hope, Cartago, Costa Rica

[73] Assignee: Ball Seed Company, West Chicago, Ill.

[21] Appl. No.: 181,893

[22] Filed: Jan. 18, 1994

[51] Int. Cl.[6] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

A new and distinct cultivar of anthurium plant named Pura Vida Lavender characterized by its lavender spathe color, pink spadix color, flowers which are held above the foliage to provide a uniform display, long lasting inflorescence, and its outwardly facing leaves which show the full leaf blade.

1 Drawing Sheet

The present invention comprises a new and distinct cultivar of Anthurium, botanically known as *Anthurium hybrid,* and referred to by the cultivar named Pura Vida Lavender.

The new cultivar is a product of a planned breeding programs carried out by the inventor in Cartago, Costa Rica. The female parent was an unnamed *Anthurium amnicola* selection, and the male parent was an unnamed cultivar *Anthurium andreanum* characterized by its small leaves. The parents are proprietary cultivars used only in the breeding program.

The new cultivar was discovered from the progeny of the stated cross by the inventor in Cartago, Costa Rica, and given the number designation 196-1. Asexual propagation by division and micropropagated leaf cuttings first carried out by or under the supervision of the inventor in Cartago, Costa Rica, and later carried out in south central Florida and West Chicago, Ill., has demonstrated that the unique features of this new anthurium are stabilized and are reproduced true to type in successive propagations.

The following observations, measurements and values describe plants grown in south central Florida in a polypropylene-covered shade house with day temperatures of 30° to 38° C. and night temperatures of 20° to 30° C. Measurements and values represent averages for six typical plants observed for evaluation purposes.

The following traits have been repeatedly observed to be characteristics which in combination distinguish the new cultivar from other Anthuriums of the same general type, for example, the unpatented but well known commercial cultivar Lady Jane to which comparative reference is made.

1. The spathe color of Pura Vida Lavender is lavender compared to the medium pink spathe color of Lady Jane.

2. The mature spadix color of the new cultivar is pink compared to the yellow-orange spadix color of Lady Jane.

3. The inflorescence is long lasting.

4. Larger flowers that are held above the foliage in a uniform and showy display.

5. The flowers of Pura Vida Lavender are flat and do not curve inwardly.

6. The leaves face outwardly showing the full leaf blade.

A detailed comparison of Pura Vida Lavender and Lady Jane appears in Chart A at the end of the specification. In general comparison, the spathe of the new cultivar is lavender in color, compared to the pinkish-red spathe color of Lady Jane. The mature spadix color of the new cultivar is pink or red-purple compared to the yellow-orange mature spadix color of Lady Jane.

All color references are to The Royal Horticultural Society Colour Chart (R.H.S.). Colors will vary somewhat depending on horticultural practices such as light level and fertilization rate, among others, without, however, any variation in genotype.

The color photographic drawing comprise a top perspective view showing the inflorescence and foliage of a typical specimen plant of the new cultivar.

The photograph is of a plant of the new cultivar grown in a 25.5 cm pot approximately 52 weeks after planting a tissue culture plug and grown under appropriate growing conditions. Colors are as accurate as possible with color illustrations of this type.

Origin: Seedling of unnamed parentage.

Classification: *Anthurium hybrid,* cv Pura Vida Lavender.

Propagation: Asexual production either by micropropagation, i.e., tissue culture, or division. Roots are initiated in approximately 22 days at 25° C. The rooting habit is epiphytic, roots emerge from stem, thick velamen.

Plant:

A. *Form.*—Upright.

B. *Habit of growth.*—Leaves produced in whorls.

C. *Foliage description.*—1. Size: a. Length: 18 cm. b. Width: 11 cm. 2. Shape: Ovate; apex is acuminate, base is truncate; leaves are held outwardly and slightly upright to perpendicular to petiole. 3. Surface texture: Leaf surfaces are smooth with veins slightly sunken on top side and protruding on under side. 4. Margin: Entire. 5. Color: a. Young foliage top side: 146A. b. Young foliage under side: 146C. c. Mature foliage top side: 147A. d. Mature foliage under side: 146B. e. Older foliage top side: 139A. f. Older foliage under side: 146B. 6. Petiole Length is 15 cm, diameter 4 mm; color 147A. 7. Venation: Color is same as top side of leaves and depends on leaf age; pattern is pinnate.

Inflorescence:

A. *Flower type and habit.*—Freely flowering.

B. *Natural flowering season.*—Year-round in tropical and subtropical areas.

C. *Flowers borne.*—Above foliage, arising from leaf axils.

D. *Penduncle.*—Length is 30 cm, diameter 4 mm; color 183B.

E. *Quantity of flowers.*—Potential of one flower per leaf.

F. *Spathe.*—1. Shape: Ovate; apex cuspidate, base truncate; spathe is attached generally perpendicular to peduncle. 2. Size: a. Length: 8.0 cm. b. Width: 4.0 cm. 3. Color: a. Young spathe top side: 62B at base 62D at tip. b. Young spathe under side: 62D. c. Mature spathe top side: 62C at base, 69B at tip. d. Mature spathe under side: 155C. e. Older spathe top side: 146D. f. Older spathe under side: 146D. 4. Surface texture: Top and under surfaces are smooth. 5. Margin: Entire.

G. *Spadix.*—1. Shape: Cylindrical, tapering upwards. 2. Size: a. Length: 4.0 cm. b. Diameter base: 7 mm. c. Diameter center: 8 mm. d. Diameter tip: 3 mm. 3. Color: a. Young spadix top: 62A. b. Young spadix base: 62A. c. Mature spadix top: 62B. d. Mature spadix base: 62C. e. Older spadix top: 144C. f. Older spadix base: 144C. 4. Ovary size: 2 mm, square. 5. Anther size: 1.5 mm, square.

Disease resistance: No fungal, bacterial or viral problems have been observed to date.

CHART A

| CHARACTERISTIC | PURA VIDA RED | LADY JANE |
|---|---|---|
| Young leaf color top side | 146A | 146A |
| Mature leaf color top side | 147A | 139A |
| Older leaf color top side | 137A | 139A |
| Young spathe color top side | 46A | 51B |
| Young spathe color under side | 46A | 51D |
| Mature spathe color top side | 46A | 51B |
| Mature spathe color under side | 46A | 51D |
| Older spathe color top side | 46A | 51C |
| Older spathe color under side | 46A | 144A |
| Spathe size width by length | 6.5 cm by 8.5 cm | 3.5 cm by 7 cm |
| Young spadix color top | 1C | 11D |
| Young spadix color base | 1C | 32C |
| Mature spadix color top | 10C | 18D |
| Mature spadix color base | 11D | 18B |
| Older spadix color top | 14D | 144A |
| Older spadix color base | 154C | 144A |

It is claimed:

1. A new and distinct cultivar of Anthurium plant named Pura Vida Lavender, as illustrated and described.

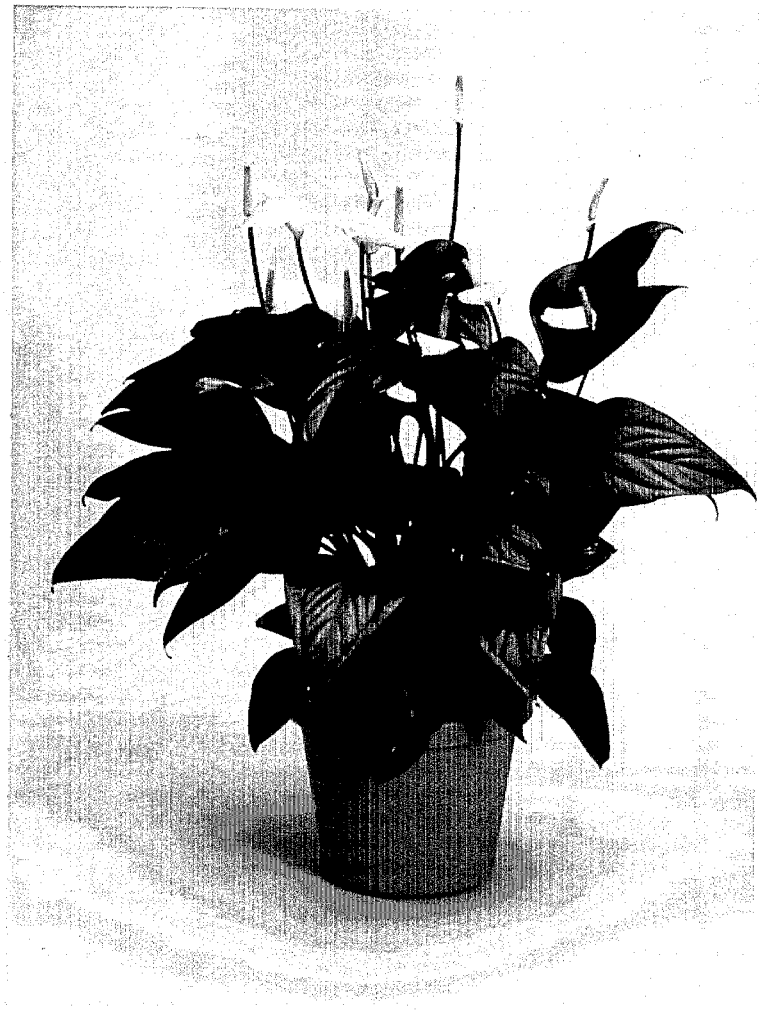

* * * * *